US006451040B1

(12) United States Patent
Purcell

(10) Patent No.: US 6,451,040 B1
(45) Date of Patent: Sep. 17, 2002

(54) ADJUSTABLE ENDCAP FOR LANCING DEVICE

(75) Inventor: D. Glenn Purcell, Edwardsburg, MI (US)

(73) Assignee: Bayer Corporation, Elkhart, NJ (US)

( * ) Notice: Subject to any disclaimer, the term of this patent is extended or adjusted under 35 U.S.C. 154(b) by 0 days.

(21) Appl. No.: 09/917,118

(22) Filed: Jul. 30, 2001

Related U.S. Application Data
(60) Provisional application No. 60/229,383, filed on Sep. 1, 2000.

(51) Int. Cl.[7] ............................................. A61B 17/14
(52) U.S. Cl. ....................... 606/181; 606/182
(58) Field of Search .................. 606/11, 181–183, 606/185, 172; 600/461, 583

(56) References Cited

U.S. PATENT DOCUMENTS

| 4,445,510 A | * | 5/1984 | Rigby ..................... 604/136 |
| 4,569,133 A | | 2/1986 | Schmidt |
| 4,759,363 A | | 7/1988 | Jensen |
| 5,133,359 A | | 7/1992 | Kedem |
| 5,318,584 A | * | 6/1994 | Lange et al. .............. 606/167 |
| 5,423,847 A | * | 6/1995 | Strong et al. .............. 606/181 |
| 5,529,581 A | | 6/1996 | Cusack |
| 5,613,978 A | | 3/1997 | Harding |
| 5,645,554 A | | 7/1997 | Hugh |
| 5,690,658 A | | 11/1997 | McAdams |
| 5,730,753 A | | 3/1998 | Morita |
| 5,916,230 A | | 6/1999 | Brenneman et al. |
| 5,954,738 A | | 9/1999 | LeVaughn et al. |
| 6,022,316 A | | 2/2000 | Eppstein et al. |
| 6,022,366 A | | 2/2000 | Schraga |
| 6,056,765 A | * | 5/2000 | Bajaj et al. .................. 606/181 |
| 6,066,103 A | * | 5/2000 | Duchon et al. ............. 600/583 |
| 6,156,050 A | * | 12/2000 | Davis et al. ................. 606/181 |
| 6,203,504 B1 | * | 3/2001 | Latterell et al. ............ 600/576 |
| 6,346,114 B1 | * | 2/2002 | Schraga ....................... 411/190 |

OTHER PUBLICATIONS

Internet website; Softclix Lancet Device, Mar. 14, 2000, 3 pgs.
Internet website; Soft Touch Lancet Device, Mar. 14, 2000, 2 pgs.
Pictures of Lancets, date unknown (at least prior to Feb. 28, 2000), 1 pg.

* cited by examiner

Primary Examiner—Michael J. Milano
Assistant Examiner—Gwen Phanijphand
(74) Attorney, Agent, or Firm—Jerome L. Jeffers

(57) ABSTRACT

An adjustable endcap for a lancing device includes a basecap and a twistcap. The basecap includes a post with detents thereon. At least one finger is provided on the basecap adjacent the post. The twistcap includes at least one helical track on its outer surface into which the finger extends when the twistcap is mounted on the post. The twistcap also includes a plurality of grooves on an inner surface for engagement with the detents. As the twistcap is rotated on the post, the interaction of the finger and track causes the twistcap to move toward and away from the basecap and to adjust the penetration depth of a lance reciprocally mounted in the lancing device.

10 Claims, 3 Drawing Sheets

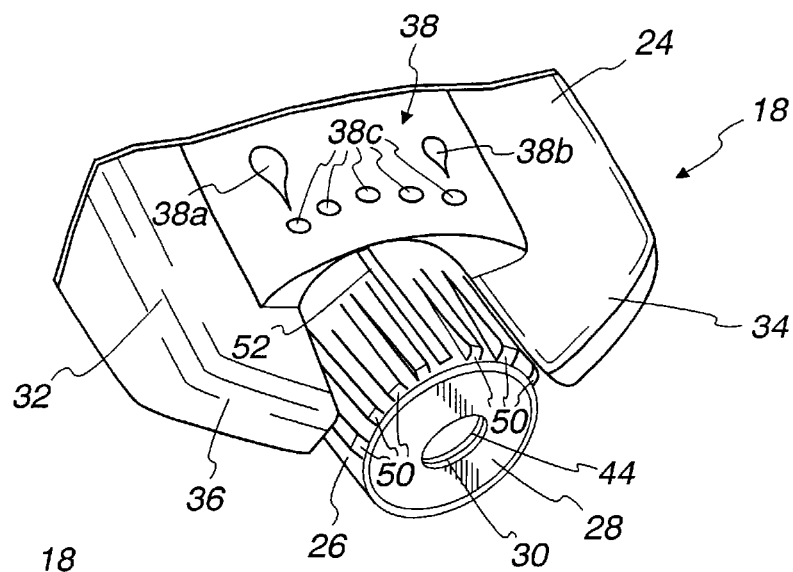
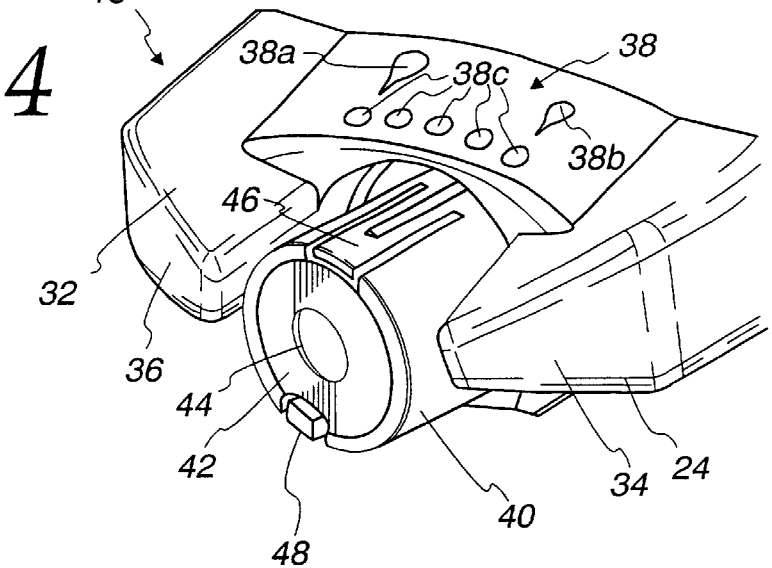
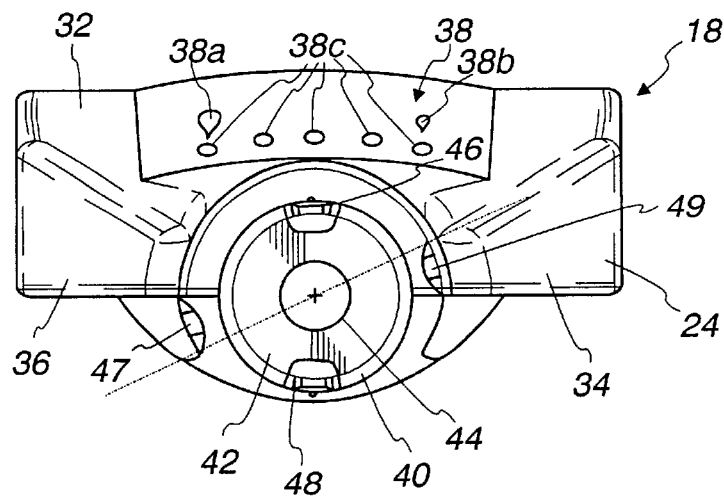

ADJUSTABLE ENDCAP FOR LANCING DEVICE this application claims the benefit of provisional application 60/229,383 filed Sep. 1, 2000.

FIELD OF THE INVENTION

The present invention relates generally to blood monitoring devices, and, more particularly, to an adjustable endcap for lancing devices used to lance a finger or other areas of the body to harvest blood for monitoring.

BACKGROUND OF THE INVENTION

It is often necessary to quickly obtain a sample of blood and perform an analysis of the blood sample. One example of a need for painlessly obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and they may eventually faint. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. In order to check the blood glucose level with the testing device, a drop of blood is obtained from the fingertip using a lancing device. A typical lancing device contains a needle lancet to puncture the skin. Some of these lancing devices have no means of adjusting the depth of penetration of the lancet. These lancing devices cannot accommodate different skin thicknesses which impacts the amount of blood that can be drawn. In addition, these devices cannot accommodate differences in pain tolerances of the person whose blood is being drawn.

Although there are adjustable lancing devices, these devices typically adjust the position of a structural element that engages a lancet holder thereby limiting the travel of the lancet. These are cumbersome to adjust and are subject to rapid deterioration. Other adjustable lancing devices have multiple parts resulting in high costs, and complicated adjustment procedures.

SUMMARY OF THE INVENTION

The present invention is an endcap for a lancing device that adjusts the penetration depth of a lancet in a lancing device allowing the lancing device to be adjusted to accommodate skin thickness and pain tolerance of the person on whom the lancing device is used. The endcap contains adjustment structure and is adapted to fit on an existing lancing device thus reducing the cost.

The endcap of the present invention consists of only two parts, a basecap and a twistcap. Because there are fewer parts than prior art adjustable lancing devices, the cost is reduced and the assembly and use of the endcap of the present invention are simplified. The basecap includes a central post on which the twistcap is mounted. The lancet of the lancing device when triggered, extends through the basecap, across the distance between the basecap and the twistcap, and through and beyond the twistcap. The end of the twistcap is the portion of the endcap that is pressed against the skin of the person from whom blood is to be drawn. The twistcap includes external helical tracks into which fingers on the basecap extend. To adjust the endcap, a user merely needs to twist or rotate the twistcap and the interaction of the fingers and helical tracks moves the twistcap relative to the basecap. The distance the lancet of the lancing device extends beyond the basecap is constant. Therefore, by adjusting the distance between the basecap and twistcap by twisting the basecap, the distance the lancet extends out of the twistcap and into a user's finger is adjusted. Consequently, the user of a lancing device that has an endcap of the present invention can easily adjust the depth of penetration of the lancet merely by rotating or twisting the endcap. There are stops that can be felt and heard by a user as the twistcap is rotated. These stops correspond to different penetration depths and are provided by detents on the central post of the basecap and detent slots on the inside of the twistcap.

BRIEF DESCRIPTION OF THE DRAWINGS

Other objects and advantages of the invention will become apparent upon reading the following detailed description in conjunction with the drawings in which:

FIG. 3 is a perspective view of the endcap for the lancing device of the present invention;

FIG. 4 is a perspective view of the endcap illustrated in FIG. 3 with the twistcap removed;

FIG. 5 is a front plan view of the endcap illustrated in FIG. 4;

DETAILED DESCRIPTION OF THE PREFERRED EMBODIMENTS

Figure 1:
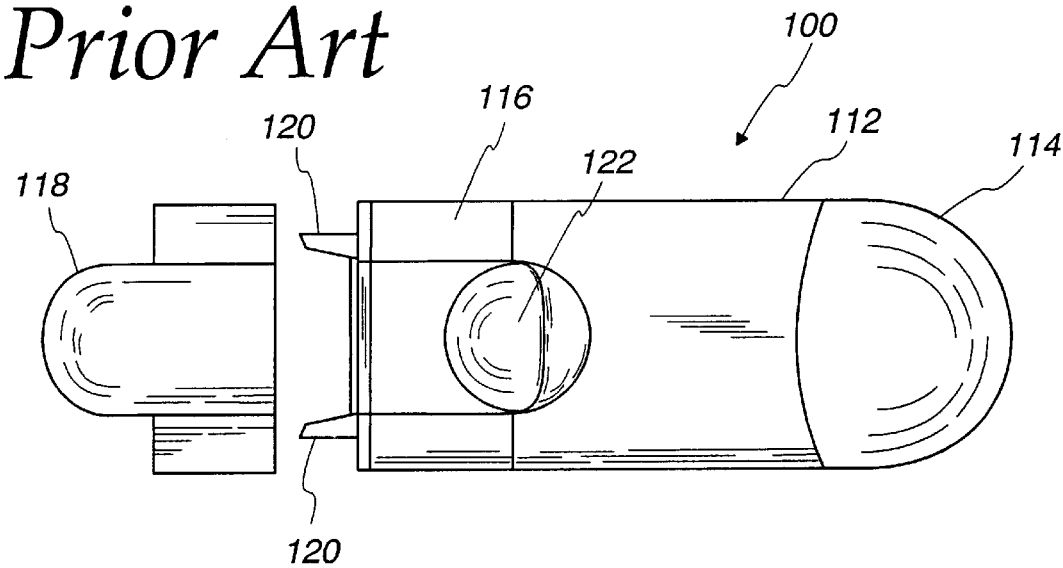
FIG. 1 is a top plan view of a prior art lancing device.
Figure 2:
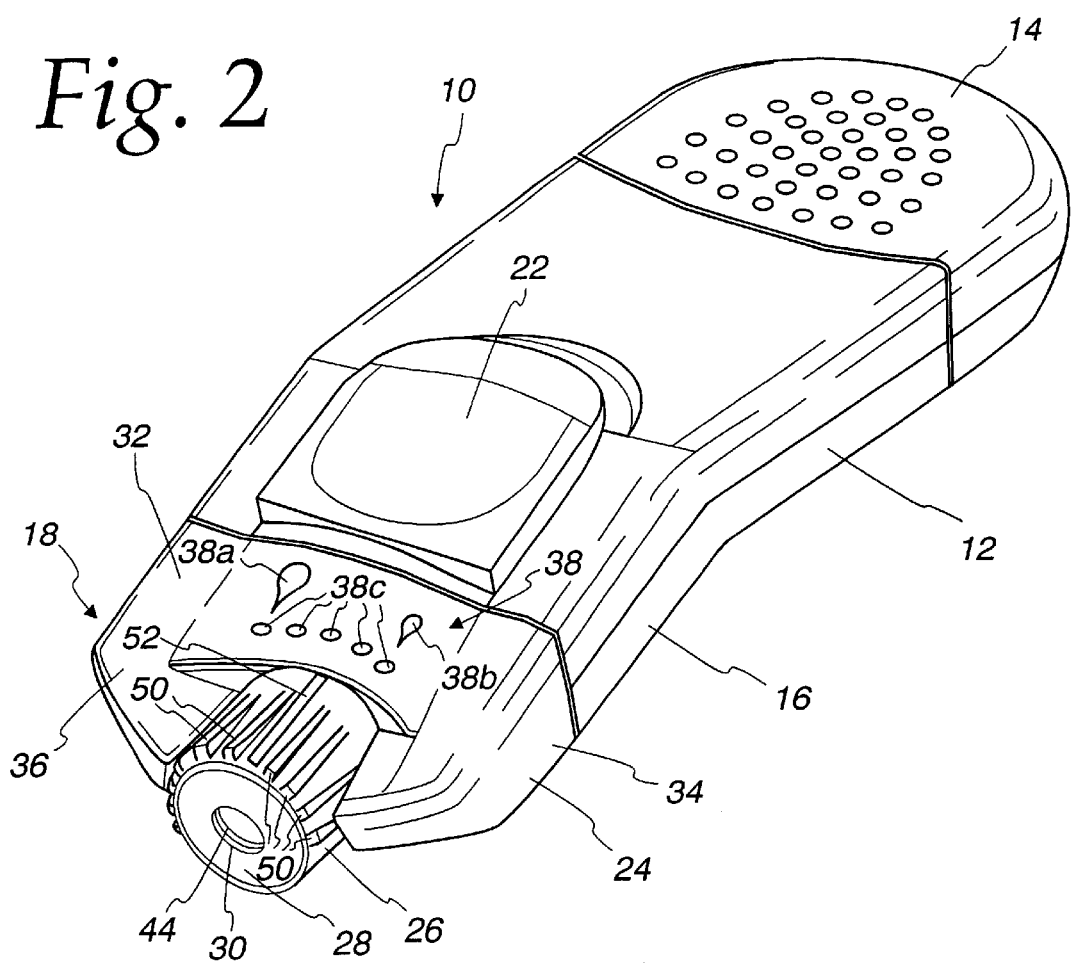
FIG. 2 is an enlarged perspective view of the lancing device of the present invention.

Many children and adults must draw their blood several times a day to perform an analysis of the blood sample drawn. Skin thickness and tolerance to pain differs among these people and a device for lancing a person's skin to draw blood preferably includes a mechanism that allows adjustment of the depth of penetration of the lance. An example of a known lancing device 100 is shown in FIG. 1. The known lancing device 100 is disclosed in U.S. Pat. No. 5,954,738 and is incorporated herein in its entirety by reference. The known lancing device 100 includes a main housing portion 112, a housing portion 114 movable relative to the main housing portion 112 and an endcap support 116. An end cap 118 may be attached onto the endcap support 116 by a pair of latching or support arms 120 which are part of the endcap support 116.

A lancing mechanism including a lance is mounted inside the main housing portion 112. The lance is driven through an opening in the endcap 118 by a driving mechanism that is cocked by pulling the housing portion 114 away from main housing portion 112. The driving mechanism is fired by pushing a button 122. The known lancing device 100 is provided with a number of different sized endcaps 118 to vary the penetration depth of the lance.

The lancing device 10 of the present invention is shown in FIGS. 2–7. The lancing device 10 is the same as the known lancing device 100 in that it includes a main housing portion 12, a housing portion 14 that is movable relative to the main housing portion, an endcap support 16 and a button 22 for firing a driving mechanism and lancing mechanism housed in the main housing portion 12. The lancing device 10 differs, however, from the known lancing device 100 in that it does not require a number of different sized endcaps to vary the penetration depth of a lance. Instead, the lancing device 10 includes an adjustable endcap 18 that can be adjusted quickly and easily for multiple lance penetration depths.

The endcap 18 is a two piece assembly consisting of a basecap 24 and a twistcap 26. The twistcap 26 includes a top or face 28 that is placed on the skin of the person whose blood is to be drawn. There is an opening 30 in the top 28 through which a lance is driven when the button 22 is depressed. By varying the position of the top 28 relative to the basecap 24, the distance the lance extends out of the twistcap 26 and thus the penetration depth of the lance can be adjusted.

To provide the lancing device 10 with quick adjustment of the penetration depth, the basecap 24 may be snapped onto a pair of support arms (not shown) similar to the support arms 120 on the known lancing device 110. As best seen in FIGS. 4 and 5, the basecap 24 includes a body 32 with a pair of shoulders 34 and 36. The shoulders 34 and 36 are hollow and fit over the support arms on the lancing device 10. Indicia 38 is provided on the top of the body 32 to indicate the different penetration depths of the lance. The basecap 24 further includes a column or post 40 located between and spaced from the shoulders 34 and 36. The post 40 includes a top 42 with a central opening 44 through which the lance extends. The post 40 also includes first 46 and second 48 cantilevered detents. A pair of protrusions or fingers 47 and 49 are formed on the inside surfaces of the shoulders 34 and 36 and extend toward the post 40.

Figure 6:
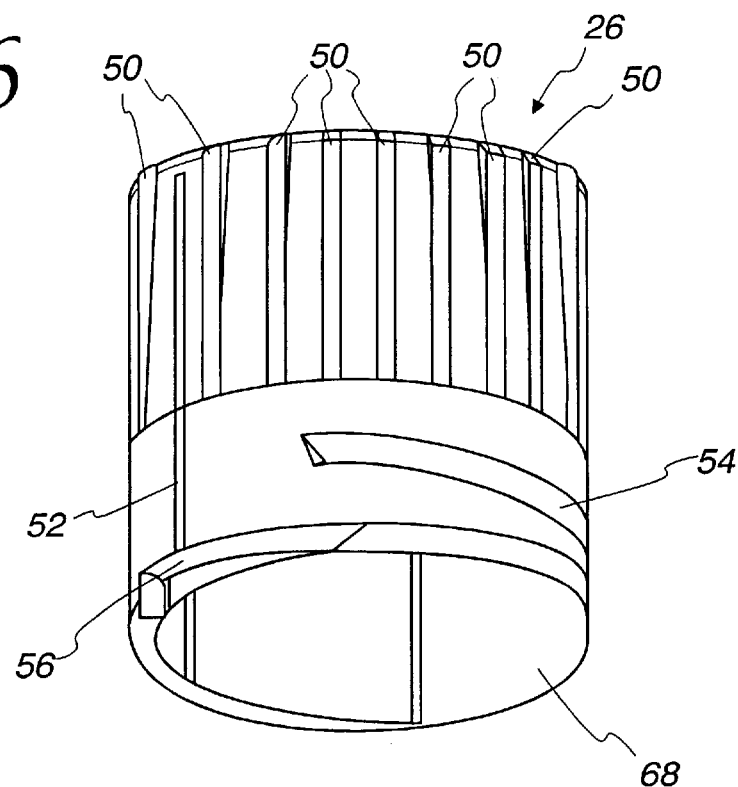
FIG. 6 is an enlarged perspective view of the twistcap.
Figure 7:
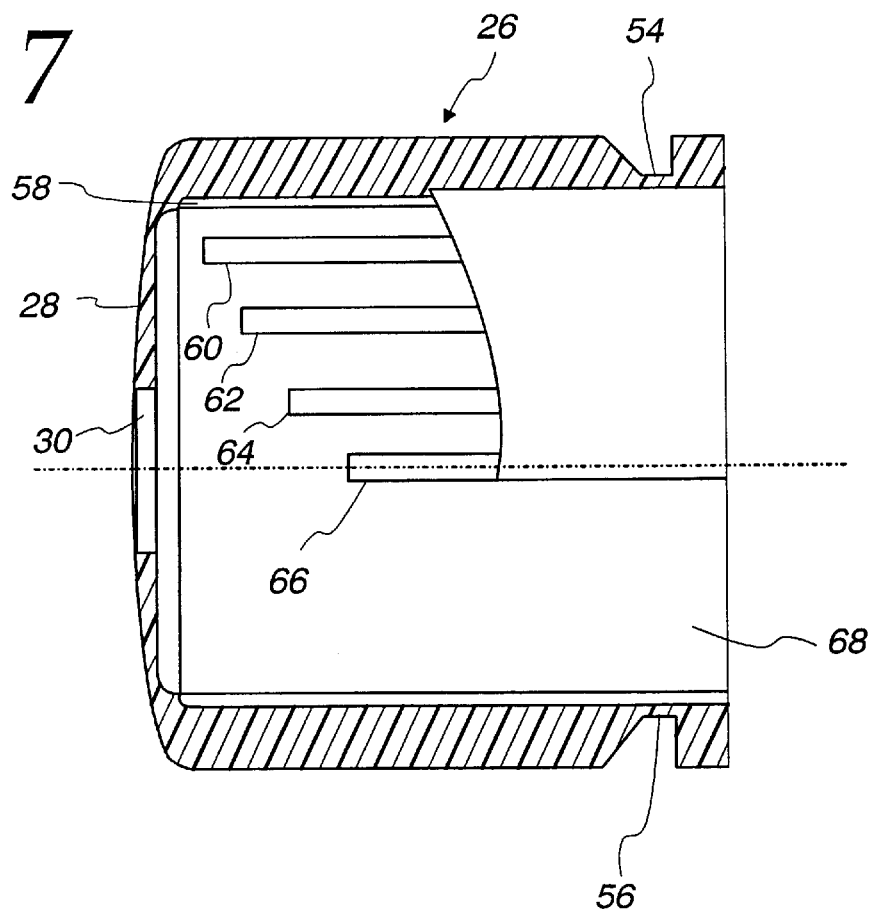
FIG. 7 is an enlarged cross sectional view of the twistcap illustrated in FIG. 6

The twistcap 26 fits over and onto the column or post 40. As best illustrated in FIGS. 3, 6 and 7, the twistcap 26 includes several ribs 50 that provide a gripping surface allowing a user to grip and rotate the twistcap 26 relative to the post 40 and the basecap 24. The twistcap 26 also includes an indicator line 52 that points to a different portion of the indicia 38 as the twistcap 26 is rotated thereby indicating the depth of penetration of the lance at that position of the twistcap 26.

A first helical groove 54 and a second helical groove 56 are formed in the lower outside surface of the twistcap 26. The grooves 54 and 56 are located on the twistcap 26 and aligned with a protrusion or finger 47 and 49 extending into a respective groove 54 and 56 when the twistcap 26 is placed on and over the post 40.

As best illustrated in FIG. 7, several slots 58, 60, 62, 64 and 66 are formed in the inner peripheral surface 68 of the twistcap 26. When the twistcap 26 is placed on the column or post 40 and rotated, the detents 46 and 48 snap into the slots 58, 60, 62, 64 and 66 to indicate to the user a specific penetration depth of the lance. In the illustrated embodiment, the indicia 38 includes a first symbol 38a in the form of a large drop and a second symbol 38b in the form of a smaller drop. Between the first symbol 38a and the second symbol 38b are five dot indicia 38c. These dot indicia 38c correspond to specific penetration depths varying from shallow (those dot indicia 38c closest to the small drop indicia 38b) to deeper (those dot indicia 38c closest to the large drop indicia 38a). A person can select the depth of penetration by twisting the twistcap to align the indicator line 52 with the dot indicia 38c that corresponds with the preferred depth of penetration.

In addition to this visual selection of the lance penetration depth, a tactile and audible indication is also provided by the detents 46 and 48 and the slots 58, 60, 62, 64 and 66. Each slot 58, 60, 62 and 64 corresponds to one of the dot indicia 38c. As a user rotates the twistcap 26 one of the detents 46 and 48 is moved out of one of the slots 58, 60, 62, 64 and 66 and the user feels a slight resistance to the rotating action. Further rotation moves the slot 58, 60, 62, 64 and 66 past the detent and the smooth inner peripheral surface 68 of the twistcap 26 passes over the detent. As the next slot 58, 60, 62, 64 or 66 passes over the detent, the detent snaps into the slot producing an audible clicking sound and the user feels a resistance to rotation. In this way the user knows when a specific penetration depth has been reached. As can be understood, adjustment of the penetration depth is easy and multiple penetration depths are possible without need to add or remove parts to the lancing device 10 or to vary the pressure by which the lancing device 10 is pressed against a user's skin.

The penetration depth of the lance is shallower the greater the distance between the face 28 of the twistcap 26 and the top 42 of the column or post 40. This distance is adjusted by the interaction of the protrusions or fingers 47 and 49 in the first and second grooves 54 and 56. As the twistcap 26 is rotated, the first and second grooves 54 and 56 are moved relative to the protrusions or fingers 47 and 49. Because the first and second grooves 54 and 56 are helical, the movement of the grooves 54 and 56 relative to the protrusions 47 and 49 causes the twistcap 26 to move longitudinally relative to the column or post 40 thereby decreasing or increasing the distance between the face 28 of the twistcap 28 and the top 42 of the column or post 40. Because the lance extends beyond the top 42 a fixed distance, as the distance between the top 42 and the top 28 is increased, the distance the lance extends beyond the top 28 is decreased, and as the distance between the top 42 and top 28 is decreased, the distance the lance extends beyond the top 28 and thus, the penetration depth, is increased.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An adjustable endcap for a lancing device, comprising:
   a basecap, and
   a twistcap,
   said basecap including a post member and at least one finger on said basecap adjacent said post member,
   said twistcap adapted to fit over said post member, said twistcap including at least one generally helical track on an outer surface thereof, said finger extending into said track when said twistcap is on said post member.

2. The adjustable endcap claimed in claim 1 comprising at least one cantilevered detent on said post member, and at least one detent receiving surface on an interior surface of said twistcap.

3. The adjustable endcap claimed in claim 1 wherein said basecap is configured to fit on a lancing device.

4. The adjustable endcap claimed in claim 1 wherein said post member is cylindrical.

5. The adjustable endcap claimed in claim 1 wherein said basecap further comprises a second finger adjacent said post and said twistcap further comprises a second generally helical track on an outer surface thereof, said second finger extending into said second track when said twistcap is on said post member.

6. An adjustable endcap for a lancing device, comprising:
   a basecap configured to be mounted on a lancing device, said basecap including a cylindrical post member with a first cantilevered detent thereon, said basecap further including a first finger adjacent to and extending radially toward said cylindrical post member; and
   a twistcap configured to fit on said cylindrical post member, a first generally helical track on an outer surface of said twistcap oriented to be aligned with said first finger when said twistcap is on said cylindrical post member, a plurality of detent receiving surfaces on an interior surface of said twistcap.

7. The adjustable endcap for a lancing device claimed in claim 6 wherein said basecap further includes a second cantilevered detent on said cylindrical post member.

8. The adjustable endcap for a lancing device claimed in claim 6 wherein said basecap further includes a second finger adjacent to and extending radially toward said cylindrical post member.

9. The adjustable endcap for a lancing device claimed in claim 6 wherein the twistcap further includes a second generally helical track on said outer surface of said twistcap.

10. An endcap for adjusting the penetration depth of a lance of a lancing device, comprising:
   a basecap including a cylindrical mounting post, first and second cantilevered detents on diametrically opposed sides of said mounting post, first and second fingers on said basecap adjacent to and on opposite sides of said mounting post; and
   a twistcap rotatably mounted on said mounting post, a plurality of detent receiving grooves on an interior surface of said twistcap, and first and second generally helical tracks formed on an outer surface of said twistcap aligned with said first and second fingers, respectively.

* * * * *

UNITED STATES PATENT AND TRADEMARK OFFICE
CERTIFICATE OF CORRECTION

PATENT NO.   : 6,451,040 B1
DATED        : September 17, 2002
INVENTOR(S)  : D. Glenn Purcell It is certified that error appears in the above-identified patent and that said Letters Patent is hereby corrected as shown below:

<u>Title page,</u>
Item [75], Inventor(s), please insert -- Christopher John Ruf, Atlanta, Georgia --.

Signed and Sealed this

Eighteenth Day of February, 2003

JAMES E. ROGAN
*Director of the United States Patent and Trademark Office*